(12) United States Patent
Michaelis

(10) Patent No.: US 7,529,670 B1
(45) Date of Patent: May 5, 2009

(54) AUTOMATIC SPEECH RECOGNITION SYSTEM FOR PEOPLE WITH SPEECH-AFFECTING DISABILITIES

(75) Inventor: Paul Roller Michaelis, Louisville, CO (US)

(73) Assignee: Avaya Inc., Basking Ridge, NJ (US)

( * ) Notice: Subject to any disclaimer, the term of this patent is extended or adjusted under 35 U.S.C. 154(b) by 543 days.

(21) Appl. No.: 11/131,108

(22) Filed: May 16, 2005

(51) Int. Cl.
*G10L 15/04* (2006.01)
*G10L 15/00* (2006.01)
*G10L 21/00* (2006.01)
*A61B 5/08* (2006.01)
*H04R 27/00* (2006.01)

(52) U.S. Cl. .................. 704/253; 704/231; 704/275; 600/538; 381/84

(58) Field of Classification Search ............. 704/253, 704/231, 275; 381/54
See application file for complete search history.

(56) References Cited

U.S. PATENT DOCUMENTS

| | | | |
|---|---|---|---|
| 4,468,804 A | 8/1984 | Kates et al. | |
| 4,696,039 A | 9/1987 | Doddington | |
| 4,852,170 A | 7/1989 | Bordeaux | |
| 5,018,200 A | 5/1991 | Ozawa | |
| 5,206,903 A | 4/1993 | Kohler et al. | |
| 5,583,969 A | 12/1996 | Yoshizumi et al. | |
| 5,684,872 A | 11/1997 | Flockhart et al. | |
| 5,828,747 A | 10/1998 | Fisher et al. | |
| 5,905,793 A | 5/1999 | Flockhart et al. | |
| 5,982,873 A | 11/1999 | Flockhart et al. | |
| 6,064,731 A | 5/2000 | Flockhart et al. | |
| 6,084,954 A | 7/2000 | Harless et al. | |
| 6,088,441 A | 7/2000 | Flockhart et al. | |
| 6,151,571 A | 11/2000 | Pertrushin | |
| 6,163,607 A | 12/2000 | Bogart et al. | |
| 6,173,053 B1 | 1/2001 | Bogart et al. | |
| 6,192,122 B1 | 2/2001 | Flockhart et al. | |
| 6,259,969 B1 | 7/2001 | Tackett | |
| 6,275,806 B1 | 8/2001 | Pertrushin | |
| 6,275,991 B1 | 8/2001 | Erlin | |

(Continued)

FOREIGN PATENT DOCUMENTS

CA    1333425    12/1994

(Continued)

OTHER PUBLICATIONS

Watson PJ, Ciccia AH, Weismer G (2003), The relation of lung volume initiation to selected acoustic properties of speech. J Acoust Soc Am 113:2812-2819.*

(Continued)

*Primary Examiner*—Richemond Dorvil
*Assistant Examiner*—Michael Ortiz Sanchez
(74) *Attorney, Agent, or Firm*—Sheridan Ross P.C.

(57) ABSTRACT

A speech recognition system is provided that, in one embodiment, includes an input 104 operable to receive voice utterances from a user, a speaker monitoring agent 132 operable to determine a pulmonary state of the user as a function of time, and a frame analyzer 120 operable to (i) determine a respective pulmonary state of the user at an approximate time when each of the voice utterances was made and (ii) process each of the voice utterance in a manner dependent upon the respective pulmonary state.

25 Claims, 2 Drawing Sheets

U.S. PATENT DOCUMENTS

| | | | |
|---|---|---|---|
| 6,278,777 | B1 | 8/2001 | Morley et al. |
| 6,292,550 | B1 | 9/2001 | Burritt |
| 6,353,810 | B1 | 3/2002 | Petrushin |
| 6,363,346 | B1* | 3/2002 | Walters ............... 704/231 |
| 6,374,221 | B1 | 4/2002 | Haimi-Cohen |
| 6,389,132 | B1 | 5/2002 | Price |
| 6,427,137 | B2 | 7/2002 | Pertrushin |
| 6,463,415 | B2 | 10/2002 | St. John |
| 6,480,826 | B2 | 11/2002 | Pertrushin |
| 6,697,457 | B2 | 2/2004 | Pertrushin |
| 6,766,014 | B2 | 7/2004 | Flockhart et al. |
| 6,889,186 | B1 | 5/2005 | Michaelis |
| 7,065,485 | B1* | 6/2006 | Chong-White et al. ...... 704/208 |
| 2002/0194002 | A1 | 12/2002 | Petrushin |
| 2002/0198707 | A1* | 12/2002 | Zhou ...................... 704/231 |
| 2004/0215453 | A1 | 10/2004 | Orbach |
| 2005/0065789 | A1* | 3/2005 | Yacoub et al. ............ 704/231 |
| 2005/0119586 | A1* | 6/2005 | Coyle et al. ............... 600/538 |
| 2006/0036437 | A1* | 2/2006 | Bushey et al. ............ 704/231 |

FOREIGN PATENT DOCUMENTS

| | | |
|---|---|---|
| EP | 0 076 687 A1 | 4/1983 |
| EP | 0 140 249 A1 | 10/1983 |
| EP | 0 360 265 A2 | 3/1990 |
| JP | 10-124089 | 5/1998 |

OTHER PUBLICATIONS

D Novak, D Cuesta-Frau, and L. Lhotska: Speech recognition methods applied to biomedical signals processing. Engineering in Medicine and Biology Society. 2004; 1: 118-121.*
M.S. Entwistle, The performance of automated speech recognition systems under adverse conditions of human exertion. Int. J. Hum.-Comput. Interact. 16 (2003) (2), pp. 127-140.*
U.S. Appl. No. 10/756,669, filed Jan. 12, 2004, Thambiratnam.
Arslan, Levent M., "Foreign Accent Classification in American English," thesis, pp. 1-200, Department of Electrical Computer Engineering, Duke University, 1996.
Arslan, Levent M., et al., "Language Accent Classification in American English," Robust Speech Processing Laboratory Department of Electrical Engineering, Durham, North Carolina, Technical Report RSPL-96-7(1996).
Hansen, John H.L., et al., "Foreign Accent Classification Using Source Generator Based Prosodic Features," IEEE Proc. ICASSP, vol. 1, Detroit U.S.A., (1995), pp. 836-839.
Hosom, John-Paul, et al., "Training Neural Networks for Speech Recognition," Center for Spoken Language Understanding, Oregon Graduate Institute of Science and Technology (Feb. 2, 1999), 51 pages.
Jackson, Philip J.B., et al., "Aero-Acoustic Modeling of Voiced and Unvoiced Fricatives Based on MRI Data," University of Birmingham and University of Southampton, (undated), 4 pages, Nov. 4, 2004.
Kirriemuri, John, "Speech Recognition Technologies," TSW 03-03 (Mar. 2003), 13 pages.
Lamel, L.F., et al., "Language Identification Using Phone-based Acoustic Likelihoods," ICASSP-94, Apr. 19-22, 1994.
Laramee, François Dominic, "Speech Interfaces for Games—Part 1: How Speech Recognition Words," GIGnews.com (2000), available at http://www.gignews.com/fdlspeech2.htm, 5 pages.
Loizou, Philip, "Speech Production and Perception," EE 6362 Lecture Notes (Fall 2000), pp. 1-30.
Markowitz, J., "Glossaries," available at http://www.jmarkowitz.com/glossary.html, 4 pages, Oct. 8, 1999.
Michaelis, Paul Roller, "Speech Digitization and Compression," Avaya Laboratories (undated), pp. 1-5.
Noth, E., et al., "Research Issues for the Next Generation Spoken"; University of Erlangen-Nuremberg, Bavarian Research Centre for Knowledge-Based Systems, at http://www5.informatik.uni-erlangen.de/literature/psdir/1999/Noeth99:RIF.ps.gz, downloaded Feb. 10, 2003.
Zue, Victor, "The MIT Oxygen Project," MIT Laboratory for Computer Science, Apr. 25-26, 2000.
"Pervasive, Human-Centered Computing," MIT Project Oxygen, MIT Laboratory for Computer Science, Jun. 2000.
"Assistive Writing," AbilityHub.com (printed Apr. 11, 2005), available at http://www.abilityhub.com/speech/speech-Id.htm, 2 pages, Feb. 24, 2001.
"Automatic Speech Recognition," Technology Access Program, AbilityHub.com (Fall 2002), available at http://tap.gallaudet.edu/SpeechRecog.htm, 2 pages.
"Contrasts in Pronunciation," available at http://www.bohemica.com/czechonline/reference/pronunciation/contrasts.htm, 2 pages, Jan. 11, 2003.
"Inside Speech Recognition," (printed Apr. 11, 2005), available at http://fsug.org/usyd.edu.au/documentation/HOWTO/Speech-Recognition-HOWTO/inside....., 2 pages, undated.
"Speech Recognition," (printed Apr. 11, 2005) available at http://murray.newcastle.edu.au/user/staff/speech/home_pages/tutorial_sr.html, 5 pages, undated.
Entwistle, "Training Methods and Enrollment Techniques to Improve the Performance of Automated Speech Recognition Systems Under Conditions of Human Exertion", A Dissertation Submitted in Partial Fulfillment of The Requirements for the Degree of Doctor of Philosophy, University of South Dakota, Jul. 2005.
U.S. Appl. No. 11/508,442, filed Aug. 22, 2006, Coughlan.
U.S. Appl. No. 11/508,477, filed Aug. 22, 2006, Michaelis.
U.S. Appl. No. 11/768,567, filed Jun. 26, 2007, Coughlan.
Agile Lie Detector; Available at: http://www.agilemobile.com/agile_liedetector.html; 2004; 1 page; Agilemobile.com.
Aviation Safety Investigation Report; Available at: http://64.233.167.104/search?q=cache:xL7YYq5EvwsJ:www.atsb.gov.au/aviation/pdf/200204328.pdf+%22speech+analysis%22+%22detect%22+and+%22state+of+intoxication%22&hl=en&gl=us&ct=clnk&cd=1; Undated; 151 pages; Australian Transport Safety Bureau, undated.
De-FIB-ulator Portable Lie Detector; Available at: http://www.sharperimage.com/us/en/catalog/product/sku_AR002; 2006; 2 pages; The Sharper Image, 2006.
Dialing Under The Influence; Available at: http://www.virginmobile.com.au/services/duti.html; 2006; 2 pages; Virgin Mobile.
Hollien H.; "Production of intoxication states by actors—acoustic and temporal characteristics."; J. Forensic Sci.; Jan. 2001; 46(1); pp. 68-73; Two-page internet summary available at http://www.ncbi.nlm.nih.gov/entrez/query.fcgi?db=pubmed&cmd=Retrieve&dopt=Abstract&list_uids=11210927&query_hl=3&itool=pubmed_ExternalLink.
Johnson K.; "Do voice recordings reveal whether a person is intoxicated? A case study."; Phonetica; 1990; 47(3-4); pp. 215-237; One-page internet summary available at http://www.ncbi.nlm.nih.gov/entrez/query.fcgi?db=pubmed&cmd=Retrieve&dopt=Abstract&list_uids=2130381&query_hl=5&itool=pubmed_ExternalLink.
Lie Detection And A Major Breakthrough In Price And Portability!; Available at: http://www.pimall.com/nais/e.pse.html; 2006; Thomas Investigative Publications, Inc.; Austin, TX.
Module 3; Available at: http://www.dendrites.com/mod3r.html; Undated; 244 pages.
Module 4, Autonomic Nervous System: Clinical Implications and Non Pharmaceutical Applications.; Available at: http://www.dendrites.com/module4.htm; Undated; 39 pages, Dec. 9, 2000.
Pisoni DB.; "Effects of alcohol on the acoustic-phonetic properties of speech: perceptual and acoustic analyses."; Alcohol Clin Exp Res.; Aug. 1989; 13(4); pp. 577-587; One-page internet summary available at http://www.ncbi.nlm.nih.gov/entrez/query.fcgi?db=pubmed&cmd=Retrieve&dopt=Abstract&list_uids=2679214&query_hl=7&itool=pubmed_ExternalLink.
Background of the above-captioned application (previously provided).

\* cited by examiner

AUTOMATIC SPEECH RECOGNITION SYSTEM FOR PEOPLE WITH SPEECH-AFFECTING DISABILITIES

FIELD

The invention relates generally to speech processing and, more particularly, to techniques for enhancing the intelligibility of processed speech.

BACKGROUND

Human speech is effected by the unique interaction of the lungs, trachea (windpipe), larynx, pharyngeal cavity (throat), oral cavity (mouth), and nasal cavity. The pharyngeal and oral cavities are known as the vocal tract. The vocal folds (cords), soft palate or velum, tongue, teeth, and lips move to different positions to produce various speech sounds and are known as articulators. Depending on the type of excitation by the larynx and lungs, two types of sounds can be produced, namely voiced and unvoiced sounds or utterances. As used herein, an "utterance" refers to any speech component that is uttered or audibly expressed by a person, including sentences, phrases, words, portions of words, and letters. Voiced speech sounds (for example, the "V" sound in "voice") are produced by tensing the vocal cords while exhaling. The tensed vocal cords briefly interrupt the flow of air, releasing it in short periodic bursts. The greater the frequency with which the bursts are released, the higher the pitch.

Unvoiced sounds (for example, the final "S" sound in "voice") are produced when air is forced past relaxed vocal cords. The relaxed cords do not interrupt the air flow; the sound is instead generated by audible turbulence in the vocal tract. A simple demonstration of the role of the vocal cords in producing voice and unvoiced sounds can be had by placing one's fingers lightly on the larynx, or voice box, while slowly saying the word "voice." The vocal cords will be felt to vibrate for the "V" sound and for the double vowel (or diphthong) "oi" but not for the final "S" sound.

Except when whispering, all vowel and nasal sounds in spoken English are voiced. Plosive sounds—also known as stops—may be voiced or unvoiced. Examples of voiced plosives include the sounds associated with "B" and "D". Examples of unvoiced plosives include the sounds associated with "P" and "T." Fricative sounds may also be voiced or unvoiced. Examples of voiced fricatives include the sounds associated with "V" and "Z." Examples of unvoiced fricatives include the sounds associated with "F" and "S."

The movement and location of the tongue, jaw, and lips are identical for the "B" and "P" sounds, the only difference being whether the sounds are voiced. The same is true of the "D" and "T" pair, the "V" and "F" pair, and the "Z" and "S" pair. For this reason, accurate detection of the presence or absence of voicing is essential in order to identify the sounds of spoken English correctly.

People having severe injuries, particularly to their cervical or thoracic spine, and people having degenerative neuromuscular diseases, such as Amyotrophic Lateral Sclerosis (also known as Lou Gehrig's Disease), can have difficulty pronouncing voiced sounds, particularly at or near the end of a breath. Such people tend to pronounce words differently depending on where they are in the breath stream. This is because, immediately after they inhale fully and begin to speak, they tend to exhale more forcefully than is the case toward the end of the breath. It is typically the case that such people generally speak softer and more rapidly toward the end of the breath stream. Consequently, though words tend to be pronounced accurately toward the beginning of the breath stream, plosives and fricatives that should be voiced are often pronounced unvoiced as the person reaches the end of the breath stream. By way of illustration, a "d" sound may be pronounced more like a "t", a "v" sound more like an "f", a "z" more like an "s", and so on.

This tendency of people with certain disabilities to pronounce the same sound differently at different degrees of lung deflation can provide substantial obstacles to their use of Automatic Speech Recognition (ASR) Systems. In ASR systems, it is common to compute "confidence levels" that are intended to indicate the likelihood that an utterance was understood correctly. When the computed confidence levels are low, it is common for systems to query the user regarding which of the "best guess" matches was correct. ASR techniques assume that a person's manner of speech remains fairly consistent from the beginning to the end of the breath stream. This assumption fails to consider that, under the same conditions, the voice characteristics of people with certain disabilities can be a moving target. Illustratively, assume that an ASR system's best guess about a spoken word is "pat" (the "p" and "t" both being unvoiced plosives). If the speaker is disabled in the manner described above and is close to the start of the exhaled breath stream, the likelihood that the intended word really is "pat" is high. This means that, in most cases at the start of the breath stream, the ASR system is correct in assuming that the utterance is "pat". However, if the utterance occurs toward the end of the breath stream, the ASR system has a much lower likelihood of being correct in assuming that the utterance is "pat" rather than "bad", "pad", or "bat". "B" and "d" are voiced plosive sounds that correspond to the unvoiced plosives "p" and "t". The inability of ASR systems to self-adjust appropriately for these individuals tends to decrease the usability and usefulness of these systems.

SUMMARY

These and other needs are addressed by the various embodiments and configurations of the present invention. The present invention is directed generally to a speech recognition system and method for effecting matching of an utterance and/or adjusting of the level of confidence of a best guess in response to a state of a user. The state may be any physical or physiological condition of the user, particularly a volume of air remaining in the user's lungs when an utterance is made. For example, the system and method can take into account that, for some people with disabilities, the level of confidence that an utterance is properly recognized by the speech recognition system varies in a predictable manner while the person is speaking, and, as a result, the system and method can self-adjust accordingly.

In a first embodiment of the present invention, a speech recognition is provided that includes the steps of:

(a) receiving a first voice utterance from a user, the first voice utterance comprising a first utterance component (the first utterance component being of a first speech type (e.g., nasals, stops or plosives, fricatives, and affricates));

(b) determining a state of the user at an approximate time when the first voice utterance was made;

(c) when the user had the first state when the first voice utterance was made, using a first algorithm to identify a potential match for the voice utterance; and (d) when the user had the second state when the first voice utterance was made, using a second different algorithm to identify a potential match for the first voice utterance.

In a second embodiment, a speech recognition method is provided that includes the steps of:

(a) receiving the voice utterance from a user;

(b) determining the state of the user at an approximate time when the voice utterance was made;

(c) when the user had a first state when the voice utterance was made, determining a first level of confidence of a selected match for the voice utterance being correct and/or comparing the first level of confidence against a first determined confidence level to determine whether to query the user for input respecting the selected match; and (d) when the user had a second state when the voice utterance was made, determining a second level of confidence of the selected match for the voice utterance being correct and/or comparing the first and/or second level of confidence against a second determined confidence level to determine whether to query the user for input respecting the selected match. The first level of confidence is normally lower than the second level of confidence, and the first determined confidence level is normally lower than the second determined confidence level.

In yet a further embodiment, a speech recognition system is provided that includes:

(a) an input operable to receive voice utterances from a user;

(b) a speaker monitoring agent operable to determine a pulmonary state of the user as a function of time; and (c) a frame analyzer operable to (i) determine the respective pulmonary state of the user at an approximate time when each of the voice utterances was made and (ii) process each voice utterance in a manner dependent upon the respective pulmonary state.

In this embodiment, the manner in which recognition confidence levels are computed is varied as a function of how much air is remaining in the speaker's lungs. In a simple configuration, the mechanism assumes that unvoiced plosives and fricatives detected toward the start of the breath stream were intended to be unvoiced; however, toward the end of the breath stream, the confidence levels reflect the fact that the user might have intended the sounds to be voiced. The amount of air remaining in the speaker's lungs can be measured by many techniques, including the use of a transducer worn on an elastic band around the speaker's chest to determine chest expansion or by estimating the amount of air remaining in the speaker's lungs by measuring the amount of time that has elapsed since the start of an utterance.

Adjusting the speech recognition operating modality as a function of how much air is remaining in a disabled person's lungs can allow the speech recognition system to respond to such persons in a more user-friendly manner than is currently possible with systems of the prior art.

In one embodiment, the speech recognition system and method are in the form of machine executable instructions stored on computer readable medium.

These and other advantages will be apparent from the disclosure of the invention(s) contained herein.

The above-described embodiments and configurations are neither complete nor exhaustive. As will be appreciated, other embodiments of the invention are possible utilizing, alone or in combination, one or more of the features set forth above or described in detail below.

As used herein, "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

DETAILED DESCRIPTION

The present invention relates to a system that is capable of significantly enhancing the accuracy of speech recognition, particularly for persons with speech-impacting disabilities. The system determines a sound type associated with individual frames of a speech signal or utterance and, when the user has a specified state, expands the number of potential matches for the utterance and/or decreases the level of confidence that the "best" match is correct. The sound type is typically unvoiced sounds. In one configuration, the manner in which recognition "confidence levels" are computed is varied as a function of how much air is remaining in the speaker's lungs. For persons with speech disabilities, particularly people having severe injuries (e.g., to their cervical or thoracic spine) and people having degenerative neuromuscular diseases (e.g., Amyotrophic Lateral Sclerosis (also known as Lou Gehrig's Disease)), the amount of air remaining in the lungs correlates closely with the forcefulness with which air is exhaled, which in turn correlates with the likelihood that specific types of mispronunciation will occur. In one approach, the inventive principles are implemented as an enhancement to well-known speech encoding algorithms, such as the Linear Predictive Coding or LPC, formant synthesis, concatenative synthesis, waveform digitization, and CELP algorithms, that perform frame-based speech digitization. The inventive principles can be used in a variety of speech applications including, for example, messaging systems, IVR applications, wireless telephone systems, speaker dependent and independent ASR systems, speaker adaptive ASR systems, and other applications involving speech recognition or command and control algorithms. For example, in a speaker dependent system the information about location-in-breath-stream when an utterance is made is a factor evaluated by the ASR system during the system-training process thereby allowing the system to better correlate the amount of air remaining in the speaker's lungs with the likelihood that certain mispronunciations will occur.

Figure 1:
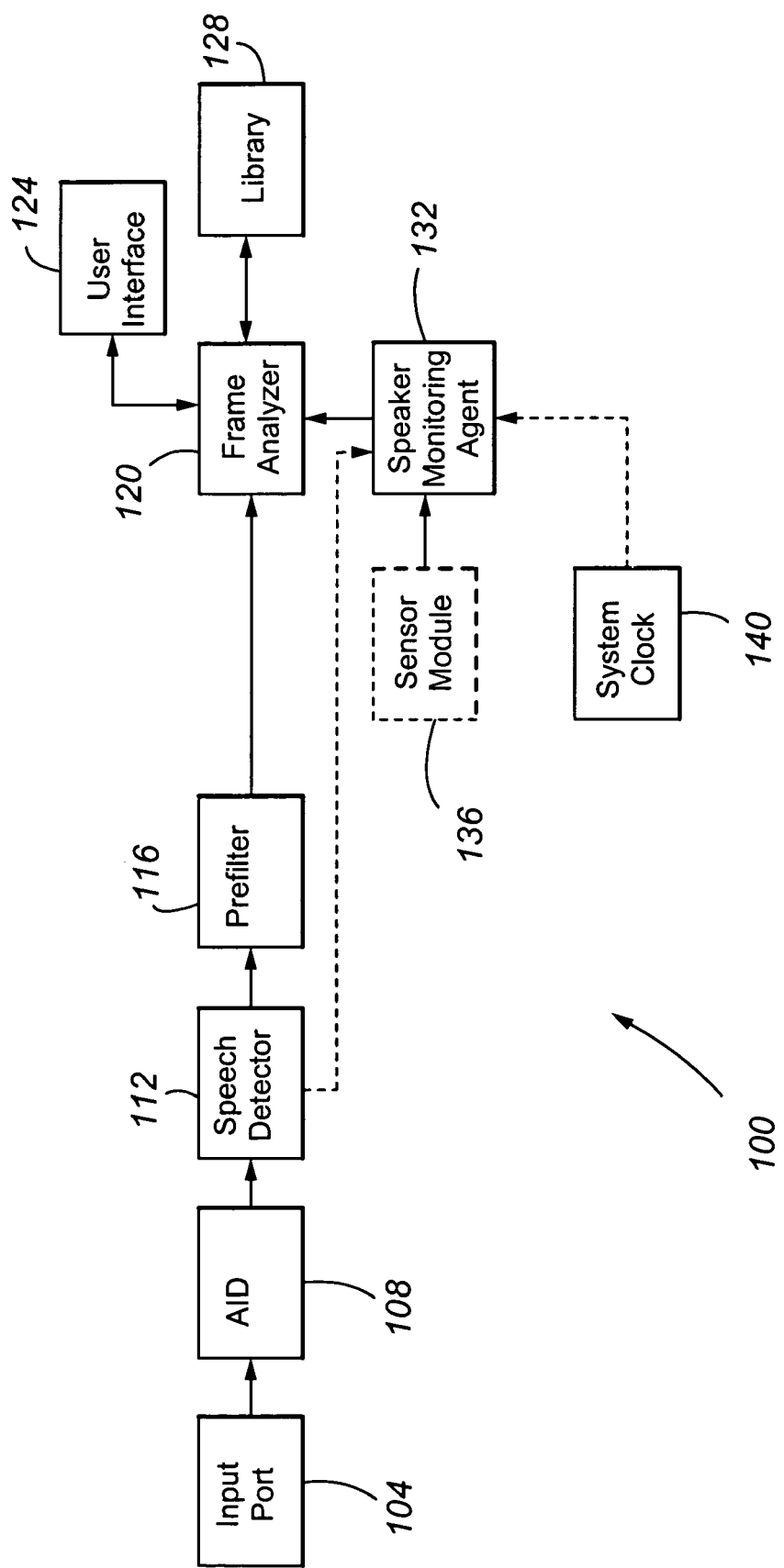
FIG. 1 is a block diagram depicting a speech recognition system according to an embodiment of the invention.

FIG. 1 is a block diagram illustrating a speech processing system 100 in accordance with one embodiment of the present invention. The speech processing system 100 receives an analog speech signal at an input port 104 (such as a microphone) and converts this signal to a text equivalent of the digital speech signal. In one configuration, the system 100 matches a sequence of observations with subword models or with word models which are built from subword models with predefined word lexicon. The recognized word or subword units are used to construct the whole word sequence with the help of language models. A continuous speech recognition system can recognize an entire sentence by first constructing a finite-state network, with or without a grammar-based language model, to represent the possible sentence model. Although the system 100 is based on a pattern recognition speech recognition approach, it is to be understood that the system may be implemented using other speech recognition approaches, such as the acoustic-phonetic or artificial intelligence approaches.

As illustrated, the speech processing system 100 includes: an analog to digital (A/D) converter 108 to convert the received audio signal it into a digital audio signal, a speech detector 112 to determine when a received audio signal includes speech, a pre-filter unit 116 to effect front-end signal processing such as pre-emphasis, blocking and windowing (or frame separation), spectral analysis, feature extraction/enhancement, normalization, banding, and/or reduction of information rate and feature dimension, a frame analysis unit 120 to effect comparison and matching against known speech samples and recognition of the speech signal, an audio and/or video user interface 124 to interact with the user, a library 128 containing matching rules (such as pronunciation and inflection rules, grammar rules, words and corresponding phonetic parameters) and/or other acoustic characterizations (such as phonemes, diphones, triphones, tetraphones, or actual recorded speech samples) and optionally exceptions thereto, a speaker monitoring agent 132 to provide the frame analyzer 120 with feedback on the state of the user, a sensor module 136 for detecting state changes in the user, and a system clock 140 to provide timing information to the agent 132 and the other system components. It should be appreciated that the blocks illustrated in FIG. 1 are functional in nature and do not necessarily correspond to discrete hardware elements. In one embodiment, for example, the speech processing system 100 is implemented within a single digital processing device. Hardware implementations, however, are also possible.

With continuing reference to FIG. 1, the analog speech signal received at port 104 is first sampled and digitized within the A/D converter 108 to generate a digital waveform for delivery to the speech detector 112. If the waveform contains an utterance, it is forwarded to the pre-filter unit 116.

The pre-filter unit 116 performs any of a number of possible operations depending on the particular system configuration. In pre-emphasis, the unit 116 pre-emphasizes the waveform in a manner determined by the speech production model. The spectrum of the waveform is normally flattened by the unit 116. In blocking and windowing, the unit 116 extracts the short-time features of the waveform by blocking the speech waveform into short segments called frames. The duration of each frame normally ranges from about 10 to about 30 ms and may contain one or more utterance components. The speech belonging to each frame is assumed to be stationary. To reduce the edge effect of each frame, a smoothing window (e.g., a Hammering window) is applied to each frame. Generally, each successive frame overlaps the next to generate a more smooth feature set over time. Each frame has a corresponding timestamp indicating when the utterance in the frame was received by the system 100. In temporal feature extraction, features of speech are extracted from each frame in the time domain. The temporal features include short-time average energy and amplitude, short-time zero-crossing rate, short-time autocorrelation, pitch periods, root mean square (rms), maximum of amplitude, voicing quality, difference between maximum and minimum values in the positive and negative halves of the signal, sound or utterance component type, and autocorrelation peaks. In spectral analysis, the waveforms in each frame are spectrally analyzed to extract spectral information of speech. Spectral analysis can be performed using any suitable algorithm such as a mel scale FFT filter-bank, perceptual linear predictive front-end, and auditory models. In extraction and enhancement of features, the obtained spectral information is processed by extracting useful features. The features in the frequency domain may include the difference between peak and valley, the energy in a particular frequency region, the spectral gradient and spectral variation contour, and the like. In reduction of information rate and feature dimension, the rate of generation of the feature vectors is reduced.

The speaker monitoring agent 132 (which is optional) provides information to the frame analyzer 120 on the state of the user at the approximate time when a selected utterance is made. The state information is received from the sensor module 136. The sensor module 136 preferably measures a pulmonary characteristic, such as the air being exhaled and/or inhaled by the user and/or the temporal lung volume of the user. The sensor module 136 can be any suitable pulmonary sensor, such as a chest-worn physical transducer, a spirometer, and the like. Alternatively, the user state information may be provided by a combination of the speech detector 112 and the system clock 140. A long pause between utterances by the user is typically synonymous with the user inhaling a breath before speaking. By detecting pauses between utterances of at least a predetermined length, the various breaths of the user and the transitions between individual exhalation and inhalation cycles can be identified. When a user starts to speak after such a pause, the assumption can be reliably made that, at the time of the initial utterance, the air volume in the user's lungs is at or near full capacity. By timing the various subsequent utterances relative to the time at which the initial utterance was made, the agent 112 can estimate the remaining amount of air in the user's lungs for each utterance or a set of utterances. The volume of air exhaled is typically a function of time and can be characterized by a suitable linear or polynomial function based on experimental observations. The foregoing process is repeated, of course, for each breath. The timing information used may be pre-configured to reflect the unique physical condition of each user. Using either approach, the agent 132 provides the frame analyzer 120 with an indicator of where the user is in the exhalation cycle or of the volume of air expelled from or remaining in the user's lungs.

The frame analyzer 120 receives the frames from the pre-filter 116 and the user state information from the agent 132 and compares and matches the waveform in each frame against library entries and thereby recognizes the speech waveform in each frame. As will be appreciated, the frame analyzer 120 may use any comparison and/or matching algorithm, whether performing discrete or isolated, continuous, or spontaneous word recognition. Examples of such algorithms include Hidden Markov Models (HMM), frequency analysis, differential analysis, linear algebra techniques/shortcuts, spectral distortion, and time distortion methods. The frame analyzer 120 generates a probability that a given match is correct, compares the probability against the predetermined level, and, when the probability is less than the predetermined level, queries the user for confirmation that the match is correct.

In one frame analyzer configuration, the frame analyzer's output depends on the state of the user while making the utterance in a selected frame and the type of utterance component in the selected frame. Each frame has a corresponding selected timestamp. This permits the analyzer 120 to determine the state of the user when a waveform in a selected frame was uttered by the user. For example, when a selected frame includes an unvoiced utterance component and the user's lungs are at least half full of air the analyzer 120 assumes that voiced and unvoiced utterance components can be reliably identified using normal pattern matching. Conversely, when the frame includes an unvoiced utterance component and the user's lungs are less than half full of air the analyzer 120 assumes that the voiced utterance components may appear to be unvoiced utterance components. In that event, the analyzer 120 expands the spectral pattern matching for each unvoiced utterance component to include not just unvoiced utterance component spectral patterns but also voiced utterance component spectral patterns. Broadening the potential matches can be filtered against words in the library 128. In other words, substituting a voiced component for an unvoiced utterance component, taken in connection with the other utterance components in a word, may produce a word that is not recognizable by the library 128. In that event, it is assumed that the unvoiced component was intended to be unvoiced. Additionally, when the user's lungs are at least half full of air the analyzer 120 determines levels of confidence as is done conventionally by ASR systems for users without disabilities. When the user's lungs are less than half full of air, the analyzer 120 can provide a reduced level of confidence for each possible match for certain types of utterance components, particularly unvoiced utterance components.

The frame analyzer 120 further provides one or more potential matches for an utterance to the user via the user interface 124 when the level of confidence for a match is less than a predetermined level. As noted, the predetermined level can be a function of the state of the user when the corresponding utterance was made or received by the system 100. The user is asked to select, by voice or tactile input, eye gaze tracking input, and/or "puff tube" input, the appropriate match from among a set of possible matches. Alternatively, the user may be asked whether a selected best guess is correct and, if not, asked to repeat the word, preferably after taking a full breath.

Figure 2:
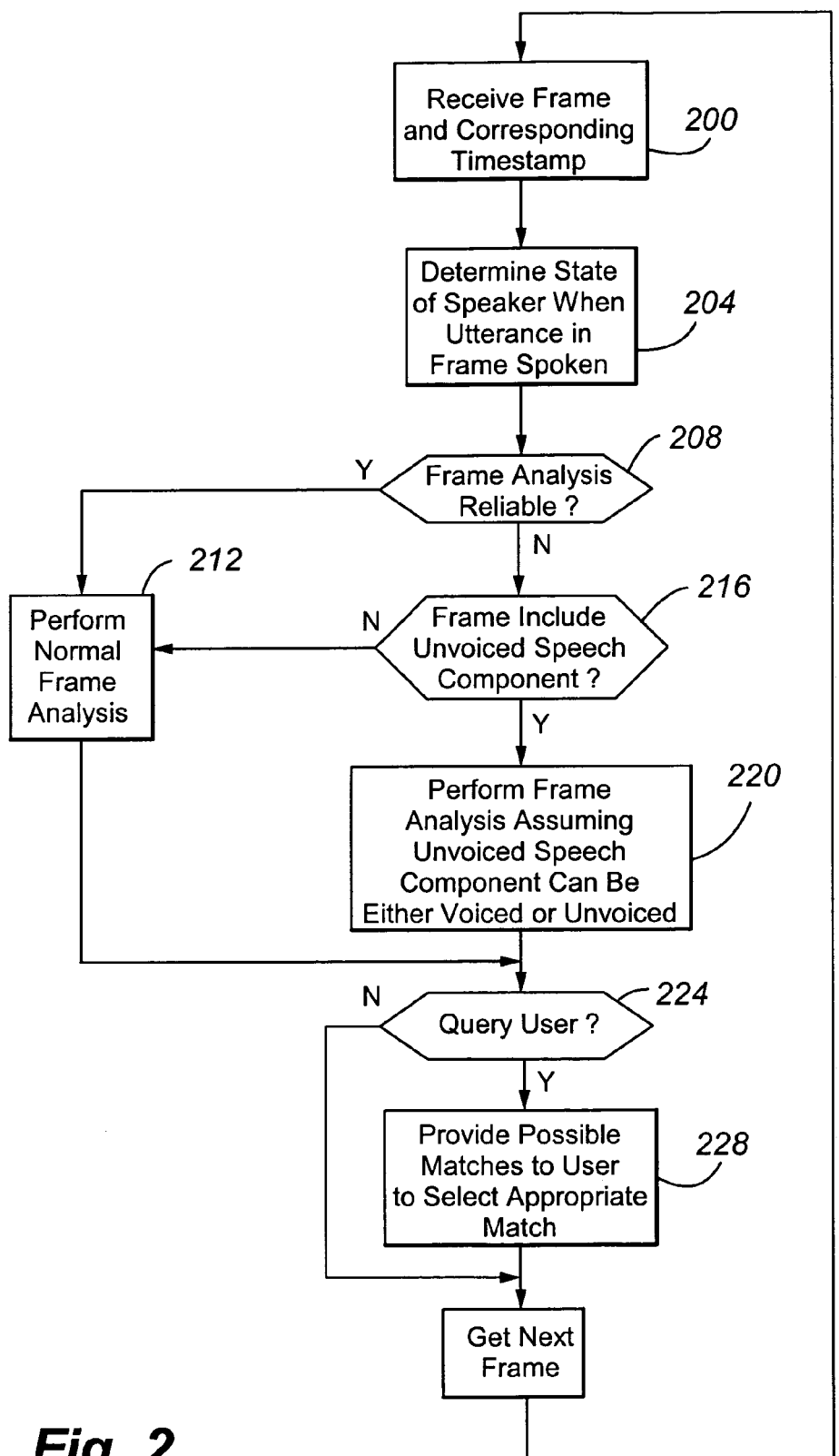
FIG. 2 is a flow chart depicting an operation of the system of FIG. 1.

An operation of the system 100 will now be described with reference to FIG. 2.

In step 200, the frame analyzer 120 receives a frame and corresponding timestamp from the pre-filter. The analyzer 120 may additionally receive an utterance component identifier indicating a type of utterance component in the frame. Typically, the type of utterance component is a voiced or unvoiced utterance component.

In step 204, the analyzer 120 queries the speaker monitoring agent 132 for the state of the user at the time corresponding to the timestamp. The state may be selected from among a set of states, e.g., lungs at least three-quarters full, lungs at least half full but less than three-quarters full, lungs at least one-quarter full but less than half full, and lungs less than one-quarter full. Alternatively, the state may be an indicator of the lung volume at the specific time of the timestamp, e.g., lungs 33% full.

In either case, the analyzer 120 determines, in decision diamond 208, whether the frame analysis can be reliably made. As shown by subsequent decision diamond 216, this determination may depend not only on the user state but also the type of utterance component in the frame. Typically, when the utterance component is not an unvoiced utterance component it is assumed that the analysis can be reliably made regardless of the user state. If a voiced utterance component is detected at any point in the exhalation cycle, there is typically a relatively high level of confidence that the component is a voiced utterance component. User state is important when the frame includes an unvoiced utterance component. In that event, the frame analysis is deemed to be reliable when the user's lungs have at least a determined amount of air remaining in them at the time of the corresponding utterance.

In any event when the frame analysis can be reliably made (decision diamond 208) or the frame fails to include an unvoiced speech component (decision diamond 212), the analyzer 120, in step 212, performs normal frame analysis.

When the frame analysis can not be reliably made (decision diamond 208) and the frame includes an unvoiced speech component (decision diamond 212), the analyzer 120, in step 220, performs frame analysis assuming that the unvoiced speech component can be either voiced or unvoiced.

After either step 212 or 220, the frame analyzer 120 determines in decision diamond 224 whether the level of confidence of a correct match is lower than the predetermined level. If so, the user is queried via user interface 124 in step 224 to disambiguate the utterance in the frame. If not or after querying the user and receiving a response, the frame analyzer 120 proceeds to step 232 and gets the next frame for analysis.

A number of variations and modifications of the invention can be used. It would be possible to provide for some features of the invention without providing others.

For example in one alternative embodiment, the ASR is trained by the user to recognize the different ways a selected voiced component is enunciated at different points during the exhalation cycle. In this manner, knowing the point in the exhalation cycle would permit the frame analyzer 120 to select the appropriate speech samples to be matched against each unvoiced or voice utterance component. This configuration, though computationally demanding, may provide more reliable matches without querying the user.

In another alternative embodiment, the various modules shown in FIG. 1 can be implemented in software, hardware (e.g., a logic circuit such as an Application Specific Circuit), or a combination thereof.

The present invention, in various embodiments, includes components, methods, processes, systems and/or apparatus substantially as depicted and described herein, including various embodiments, subcombinations, and subsets thereof. Those of skill in the art will understand how to make and use the present invention after understanding the present disclosure. The present invention, in various embodiments, includes providing devices and processes in the absence of items not depicted and/or described herein or in various embodiments hereof, including in the absence of such items as may have been used in previous devices or processes, e.g., for improving performance, achieving ease and\or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover, though the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A speech recognition method, comprising:
   (a) receiving, by an input port, a first voice utterance from a user, the first voice utterance comprising at least a first utterance component;
   (b) determining, by speaker monitoring agent, a pulmonary state of the user at an approximate time when the first voice utterance was made, wherein the first and second pulmonary states indicate at least one of an amount of air in the user's lungs, a degree of expansion of the user's lungs, and a forcefulness with which air is exhaled;
   (c) applying, by a frame analyzer, the following rules:
      (C1) when the user had a first pulmonary state when the first voice utterance was made, using a first algorithm to identify a potential match for the voice utterance; and
      (C2) when the user had a second pulmonary state when the first voice utterance was made, using a second different algorithm to identify a potential match for the first voice utterance.

2. The method of claim 1, wherein, when rule (C1) applies, further comprising the step:
   comparing the first voice utterance against a first set of set of language components assuming that the first utterance component is of a first speech type and comparing the first utterance against a second set of language components assuming that the first utterance component is of a second speech type; and
   wherein, when rule (C2) applies, further comprising the step:
   comparing the first voice utterance against a first set of set of language components assuming that the first utterance component is of the first speech type without assuming that the first utterance component is of the second speech type.

3. The method of claim 2, wherein in the first pulmonary state the user's lungs are less than half full of air and in the second pulmonary state the user's lungs are more than half full of air.

4. The method of claim 3, wherein the first speech type is an unvoiced sound and the second speech type is a voiced sound.

5. The method of claim 4, wherein the determining step comprises the substep:
   sensing at least one of a degree of chest expansion at a selected time, an amount of air in the user's lungs at the selected time, and an air volume exhaled by the user over a selected time interval including the selected time.

6. The method of claim 4, wherein the determining step (b) comprises the substeps:
   (B1) identifying the occurrence of an inhalation cycle by the user;
   (B2) identifying a first timing of the first utterance by the user following the identified inhalation cycle;
   (B3) determining a second timing of a second utterance by the user, the first and second utterances being spoken during exhalation of a common breath; and
   (B4) determining a pulmonary state of the user at the second timing based on the time interval between the first and second timings.

7. A computer readable medium encoded with processor-executable instructions that, when executed, perform the steps of claim 1.

8. The method of claim 1, wherein the first and second algorithms provide differing levels of confidence for a potential match and wherein the first and second states indicate, at the approximate time, an amount of air remaining in the user's lungs.

9. The method of claim 1, wherein the first and second states reflect a pulmonary state of the user and wherein step (b) comprises the substep:
   (B1) detecting a pause of at least a predetermined length between temporally adjacent utterances of the user, the detected pause being assumed to be associated with a transition between temporally adjacent inhalation and exhalation cycles, wherein the approximate time is measured relative to a selected part of the pause based on the assumption that, at the selected part of the pause, the user's lungs are at or near full capacity.

10. The method of claim 1, wherein the first and second pulmonary states indicate at least one of an amount of air in and a degree of expansion of the user's lungs.

11. A speech recognition method, comprising:
    (a) receiving, by an input, a voice utterance from a user, the voice utterance comprising at least a first utterance component, wherein the first utterance component is of a first speech type;
    (b) determining, by a speaker monitoring agent, a state of the user at an approximate time when the voice utterance was made;
    (c) applying, by a frame analyzer, the following rules:
       (C1) when the user had a first state when the voice utterance was made, at least one of (i) determining a first level of confidence of a selected match for the voice utterance being correct and (ii) comparing the first level of confidence against a first determined confidence level to determine whether to query the user for input respecting the selected match; and
       (C2) when the user had a second state when the voice utterance was made, at least one of (i) determining a second level of confidence of the selected match for the voice utterance being correct and (ii) comparing the first and/or second level of confidence against a second determined confidence level to determine whether to query the user for input respecting the selected match, wherein the first level of confidence is different from the second level of confidence and the first determined confidence level is different from the second determined confidence level;
    wherein the first and second states indicate at least one of an amount of air in and a degree of expansion of the user's lungs.

12. The method of claim 11, wherein the first level of confidence is lower than the second level of confidence and the first determined confidence level is lower than the second determined confidence level.

13. The method of claim 11, further comprising applying the following rules:
    (C3) when the user had a first state when the voice utterance was made, using a first algorithm to identify a potential match for the voice utterance; and
    (C4) when the user had a second state when the voice utterance was made, using a second different algorithm to identify a potential match for the voice utterance.

14. The method of claim 11, wherein when rule (C1) applies further comprising the step:
    comparing the voice utterance against a first set of set of language components assuming that the first utterance component is of the first speech type and comparing the utterance against a second set of language components assuming that the first utterance component is of a second speech type; and wherein when rule (C2) applies further comprising the step:

comparing the voice utterance against a first set of set of language components assuming that the first utterance component is of the first speech type without assuming that the first utterance component is of the second speech type.

15. The method of claim 14, wherein the first speech type is an unvoiced sound and the second speech type is a voiced sound.

16. The method of claim 11, wherein the determining step (b) comprises the substep:

sensing at least one of a degree of chest expansion at a selected time, an amount of air in the user's lungs at the selected time, and an air volume exhaled by the user over a selected time interval including the selected time.

17. The method of claim 11, wherein the determining step (b) comprises the substeps:

(B1) identifying the occurrence of an inhalation cycle by the user;

(B2) identifying a first timing of a first utterance by the user following the identified inhalation cycle;

(B3) determining a second timing of a second utterance by the user, the first and second utterances being spoken during exhalation of a common breath; and (B4) determining a pulmonary state of the user at the second timing based on the time interval between the first and second timings.

18. A computer readable medium encoded with processor-executable instructions that, when executed, perform the steps of claim 11.

19. A speech recognition system comprising:

(a) an input for receiving voice utterances from a user;

(b) a speaker monitoring agent for determining a pulmonary state of the user as a function of time, wherein the first and second pulmonary states indicate at least one of an amount of air in the user's lungs, a degree of expansion of the user's lungs, and a forcefulness with which air is exhaled; and (c) a frame analyzer for (i) determining a respective pulmonary state of the user at an approximate time when each of the voice utterances was made and (ii) processing each voice utterance in a manner dependent upon the respective pulmonary state.

20. The speech recognition system of claim 19, wherein the frame analyzer is operable, when the user had a first state when a selected voice utterance was made, to use a first algorithm to identify a potential match for the voice utterance and, when the user had a second state when a selected voice utterance was made, to use a second different algorithm to identify a potential match for the voice utterance.

21. The speech recognition system of claim 20, wherein, when the user had a first state when a selected voice utterance was made, the frame analyzer is operable to at least one of (i) determine a first level of confidence of a selected match for the selected voice utterance being correct and (ii) compare the first level of confidence against a first determined confidence level to determine whether to query the user for input respecting the selected match and, when the user had a second state when the selected voice utterance was made, at least one of (i) determine a second level of confidence of the selected match for the selected voice utterance being correct and (ii) compare the first and/or second level of confidence against a second determined confidence level to determine whether to query the user for input respecting the selected match, wherein the first level of confidence is lower than the second level of confidence and the first determined confidence level is lower than the second determined confidence level.

22. The speech recognition system of claim 19, wherein a first voice utterance comprises at least a first utterance component, wherein the first utterance component is of a first speech type and wherein the speech analyzer is operable, when the user had a first state when the first voice utterance was made, to use a first algorithm to identify a potential match for the first voice utterance and, when the user had a second state when the first voice utterance was made, to use a second different algorithm to identify a potential match for the first voice utterance.

23. The speech recognition system of claim 22, wherein, depending on the pulmonary state, the frame analyzer operates in either a first or second mode and wherein the first mode comprises the suboperation of:

comparing the first voice utterance against a first set of set of language components assuming that the first utterance component is of the first speech type and comparing the first utterance against a second set of language components assuming that the first utterance component is of a second speech type; and wherein the second mode comprises the suboperation of:

comparing the first voice utterance against a first set of set of language components assuming that the first utterance component is of the first speech type without assuming that the first utterance component is of the second speech type.

24. The speech recognition system of claim 23, wherein the first and second states indicate at least one of an amount of air in and a degree of expansion of the user's lungs.

25. The speech recognition system of claim 23, wherein the first speech type is an unvoiced sound and the second speech type is a voiced sound.

\* \* \* \* \*